US008088899B2

(12) United States Patent
Koh (10) Patent No.: US 8,088,899 B2
(45) Date of Patent: Jan. 3, 2012

(54) HUMAN GRANULOCYTE-COLONY STIMULATING FACTOR ISOFORMS

(75) Inventor: Hyung Kon Koh, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 351 days.

(21) Appl. No.: 11/917,335

(22) PCT Filed: Jun. 13, 2006

(86) PCT No.: PCT/KR2006/002238
§ 371 (c)(1),
(2), (4) Date: Oct. 2, 2009

(87) PCT Pub. No.: WO2006/135176
PCT Pub. Date: Dec. 21, 2006

(65) Prior Publication Data
US 2010/0143288 A1 Jun. 10, 2010

(30) Foreign Application Priority Data
Jun. 13, 2005 (KR) ........................ 10-2005-0050608

(51) Int. Cl.
*A61K 38/24* (2006.01)
*C07K 1/00* (2006.01)
*C07K 14/00* (2006.01)
(52) U.S. Cl. ..................... 530/399; 530/402; 530/350
(58) Field of Classification Search ................ None
See application file for complete search history.

(56) References Cited

U.S. PATENT DOCUMENTS

| 4,179,337 | A | 12/1979 | Davis et al. ................... 435/181 |
| 4,904,584 | A | 2/1990 | Shaw ........................... 435/69.4 |
| 5,166,322 | A | 11/1992 | Shaw et al. ..................... 530/351 |
| 5,206,344 | A | 4/1993 | Katre et al. ..................... 530/351 |
| 5,214,132 | A | 5/1993 | Kuga et al. ..................... 530/351 |
| 5,218,092 | A | 6/1993 | Sasaki et al. ................... 530/351 |
| 5,362,853 | A | 11/1994 | Kuga et al. ..................... 530/351 |
| 5,416,195 | A | 5/1995 | Camble et al. ................. 530/351 |
| 5,581,476 | A | 12/1996 | Osslund ........................... 702/19 |
| 5,766,897 | A | 6/1998 | Braxton ......................... 435/463 |
| 5,824,784 | A | 10/1998 | Kinstler ........................ 530/399 |
| 5,824,887 | A | 10/1998 | Baumlin ....................... 73/64.48 |
| 6,555,660 | B2 | 4/2003 | Nissen et al. ................. 530/397 |
| 6,753,165 | B1 | 6/2004 | Cox et al. ..................... 435/69.51 |
| 2002/0004483 | A1 | 1/2002 | Nissen et al. |
| 2003/0158375 | A1 | 8/2003 | Nissen et al. ................. 530/300 |
| 2003/0171559 | A1 | 9/2003 | Osslund ........................ 530/397 |
| 2004/0084884 | A1 | 5/2004 | Yamazaki et al. ............... 280/71 |
| 2004/0175800 | A1 | 9/2004 | Cox, III ....................... 435/69.4 |
| 2004/0214287 | A1 | 10/2004 | Cox, III ........................ 435/69.5 |
| 2005/0058621 | A1 | 3/2005 | Cox, III ........................ 424/85.1 |

FOREIGN PATENT DOCUMENTS

| EP | 0335423 | 8/1995 |
| EP | 0401384 | 3/1996 |
| KR | 2002/0007297 | 1/2002 |
| KR | 2002/0079778 | 10/2002 |
| KR | 2004/0084884 | 10/2004 |
| WO | WO 94/20069 | 9/1994 |
| WO | WO 95/21629 | 8/1995 |
| WO | WO 96/11953 | 4/1996 |
| WO | WO 00/42175 | 7/2000 |
| WO | WO 01/51510 A2 | 7/2001 |
| WO | WO 02/19766 | 2/2002 |

OTHER PUBLICATIONS

Welte et al., "Purification and biochemical characterization of human pluripotent Hematopoietic colony-stimulating factor," *PNAS*, 1985, 82, 1526-1530.
Souza et al., "Recombinant Human Granulocyte Colony-Stimulating Factor: Effects on Normal and Leukemic Myeloid Cells," *Science*, 1986, 232, 61-65.
Nagata et al., "Molecular cloning and expression of cDNA for human granulocyte colony-stimulating factor," *Nature*, 1986, 319, 415-418.
Horan et al., "Dimerization of the Extracellular Domain of Granulocyte-Colony Stimulating Factor Receptor by Ligand Binding: A monovalent Ligand Induces 2:2 Complexes," *Biochemistry*, 1996, 35, 4886-4896.
Aritomi et al., "Atomic structure of the GCSF-receptor complex showing a new cytokine-receptor recognition scheme," *Nature*, 1999, 401, 713-717.
Layton et al., "Identification of Ligand-binding Site III on the Immunoglobulin-like Domain of the Granulocyte Colony-stimulating Factor Receptor," *J. Biol. Chem.*, 2001, 276(39), 36779-36787.
Satake-Ishikawa et al., "Chemical Modification of Recombinant Human Granulocyte Colony-Stimulating Factor by Polyethylene Glycol Increases its Biological Activity in vivo," *Cell Structure and Function*, 1992, 17, 157-160.
Layton et al., "Interaction of Granulocyte Colony-stimulating Factor (G-CSF) with Its Receptor," *J. Biol. Chem.*, 1999, 274(25), 17445-17451. Sarkar et al., "Cell-Level Pharmacokinetic Model of Granulocyte Colony-Stimulating Factor: Implications for Ligand Lifetime and Potency in Vivo," *Mol. Pharmacol.*, 2003, 63(1), 147-158.
Sarkar et al., "Rational cytokine design for increased lifetime and enhanced potency using pH-activated "histidine switching"," *Nature Biotech.*, 2002, 20, 908-913.
Knauf et al., "Relationship of Effective Molecular Size to Systematic Clearence in Rats of Recombinant Interleukin-2 Chemically Modified with Water-soluble Polymers," *J. Hiol. Chem.*, 1998, 263(29), 15064-15070.
Ishii et al., "Effects of the state of the succinimido-ring on the fluorescence and structural properties of pyrene maleimide-labled αα-Tropomyosin," *Biophys. J.*, 1986, 50, 75-80.
Gurd, F.R.N., "[34a] Carboxymethylation," Method Enzymol, 1972, B25, 424-449.
Woghiren et al., "Protected Thiol-Polytehylene Glycol: A New Acticated Polymer for Reversible Protein Modification," *Bioconjugate Chem.*, 1993, 4, 314-318.
Rich et al., "Alkylating Derivatives of Amino Acids and Peptides. Synthesis of N-Maleoyalamino Acids,[1] [1-(N-Maleoyglycyl)cysteinyl]oxytocin, and [1-(N-Maleoyl-11-aminoundecanoyl)cysteinyl[oxytocin. Effects on Vasopressin-Stimulated Water Loss from Isolated Toad Bladder," *J. Med. Chem.*, 1975, 18(10), 1004-1010.

*Primary Examiner* — Shulamith H Shafer
(74) *Attorney, Agent, or Firm* — Woodcock Washburn LLP (57) ABSTRACT

Disclosed is a novel physiologically active protein, which is a human granulocyte colony stimulating factor isoform, constructed in order to increase the in vivo lifetime of human granulocyte colony sedtimulating factor. The human granulocyte colony stimulating factor isoform comprises a polypeptide and polyethylene glycol (PEG) bound thereto as a non-protein polymer. A specific site of the polypeptide is selected so that polyethylene can be bound to the site while not adversely affecting the activity of the protein. The amino acid of the site is modified with cysteine and polyethylene glycol is bound to the modified site. A pharmaceutical composition comprising the isoforms, genes encoding the isoforms, and a primer for modifying the amino acid sequence are also disclosed.

4 Claims, 3 Drawing Sheets

[Fig. 1]

```
                                        TC TAG AAA AAA CCA AGG AGG TAA TAA ATA
                                        AG ATC TTT TTT GGT TCC TCC ATT ATT TAT 1                                          10                                         20
Met Thr Pro Leu Gly Pro Ala Ser Ser Leu Pro Gln Ser Phe Leu Leu Lys Cys Leu Glu Gln
ATG ACT CCA TTA GGT CCT GCT TCT TCT CTC CCG CAA AGC TTT CTG CTG AAA TGT CTG GAA CAG
TAC TGA GGT AAT CCA GGA CGA AGA AGA GAC GGC GTT TCG AAA GAC GAC TTT ACA GAC CTT GTC 30                                         40
      Val Arg Lys Ile Gln Gly Asp Gly Ala Ala Leu Gln Glu Lys Leu Cys Ala Thr Tyr Lys
      GTT CGT AAA ATC CAG GGT GAC GGT GCT GCA CTG CAA GAA AAA CTG TGC GCT ACT TAC AAA
      CAA GCA TTT TAG GTC CCA CTG CCA CGA CGT GAC GTT CTT TTT GAC ACG CGA TGA ATG TTT 50                                         60
      Leu Cys His Pro Glu Glu Leu Val Leu Leu Gly His Ser Leu Gly Ile Pro Trp Ala Pro
      CTG TGC CAT CCG GAA GAG CTG GTA CTG CTG GGT CAT TCT CTT GGT ATC CCG TGG GCT CCG
      GAC ACG GTA GGC CTT CTC GAC CAT GAC GAC CCA GTA AGA GAA CCA TAG GGC ACC CGA GGC 70                                         80
      Leu Ser Ser Cys Pro Ser Gln Ala Leu Gln Leu Ala Gly Cys Leu Ser Gln Leu His Ser
      CTG TCT TCT TGT CCA TCT CAA GCT CTT CAG CTG GCT GGT TGT CTG TCT CAA CTG CAT TCT
      GAC AGA AGA ACA GGT AGA GTT CGA GAA GTC GAC CGA CCA ACA GAC AGA GTT GAC GTA AGA 90                                        100
      Gly Leu Phe Leu Tyr Gln Gly Leu Leu Gln Ala Leu Glu Gly Ile Ser Pro Glu Leu Gly
      GGT CTG TTC CTG TAT CAG GGT CTT CTG CAA GCT CTG GAA GGT ATC TCT CCG GAA CTG GGT
      CCA GAC AAG GAC ATA GTC CCA GAA GAC GTT CGA GAC CTT CCA TAG AGA GGC CTT GAC CCA 110                                        120
      Pro Thr Leu Asp Thr Leu Gln Leu Asp Val Ala Asp Phe Ala Thr Thr Ile Trp Gln Gln
      CCG ACT CTG GAC ACT CTG CAG CTA GAT GTA GCT GAC TTT GCT ACT ACT ATT TGG CAA CAG
      GGC TGA GAC CTG TGA GAC GTC GAT CTA CAT CGA CTG AAA CGA TGA TGA TAA ACC GTT GTC 130                                        140
      Met Glu Glu Leu Gly Met Ala Pro Ala Leu Gln Pro Thr Gln Gly Ala Met Pro Ala Phe
      ATG GAA GAG CTC GGT ATG GCA CCA GCT CTG CAA CCG ACT CAA GGT GCT ATG CCG GCA TTC
      TAC CTT CTC GAG CCA TAC CGT GGT CGA GAC GTT GGC TGA GTT CCA CGA TAC GGC CGT AAG 150                                        160
      Ala Ser Ala Phe Gln Arg Arg Ala Gly Gly Val Leu Val Ala Ser His Leu Gln Ser Phe
      GCT TCT GCA TTC CAG CGT CGT GCA GGA GGT GTA CTG GTT GCT TCT CAT CTC CAA TCT TTC
      CGA AGA CGT AAG GTC GCA GCA CGT CCT CCA CAT GAC CAA CGA AGA GTA GAC GTT AGA AAG

170
      Leu Glu Val Ser Tyr Arg Val Leu Arg His Leu Ala Gln Pro
      CTG GAA GTA TCT TAC CGT GTT CTG CGT CAT CTG GCT CAG CCG TAA TAG AAT TCG GAT CCCG
      GAC CTT CAT AGA ATG GCA CAA GAC GCA GTA GAC CGA GTC GGC ATT ATC TTA AGC CTA GGGC
```

[Fig. 2]

```
          1                                          10                                         20
Met (AA)n Thr Pro Leu Gly Pro Ala Ser Ser Leu Pro Gln Ser Phe Leu Leu Lys Cys Leu Glu Gln 30                                         40
      Val Arg Lys Ile Gln Gly Asp Gly Ala Ala Leu Gln Glu Lys Leu Cys Ala Thr Tyr Lys 50                                         60
      Leu Cys His Pro Glu Glu Leu Val Leu Leu Gly His Ser Leu Gly Ile Pro Trp Ala Pro 70                                         80
      Leu Ser Ser Cys Pro Ser Gln Ala Leu Gln Leu Ala Gly Cys Leu Ser Gln Leu His Ser 90                                        100
      Gly Leu Phe Leu Tyr Gln Gly Leu Leu Gln Ala Leu Glu Gly Ile Ser Pro Glu Leu Gly 110                                        120
      Pro Thr Leu Asp Thr Leu Gln Leu Asp Val Ala Asp Phe Ala Thr Thr Ile Trp Gln Gln 130                                        140
      Met Glu Glu Leu Gly Met Ala Pro Ala Leu Gln Pro Thr Gln Gly Ala Met Pro Ala Phe 150                                        160
      Ala Ser Ala Phe Gln Arg Arg Ala Gly Gly Val Leu Val Ala Ser His Leu Gln Ser Phe

170
      Leu Glu Val Ser Tyr Arg Val Leu Arg His Leu Ala Gln Pro
```

[Fig. 3]

```
  1                                                         10                                                         20
Met Thr Pro Leu Gly Pro Ala Ser Ser Leu Pro Gln Ser Phe Leu Leu Lys Cys Leu Glu Gln
                                                            30                                                         40
    Val Arg Lys Ile Gln Gly Asp Gly Ala Ala Leu Gln Glu Lys Leu Cys Ala Thr Tyr Lys
                                                            50                                                         60
    Leu Cys His Pro Glu Glu Leu Val Leu Leu Gly His Ser Leu Gly Ile Pro Trp Ala Pro
                                                            70                                                         80
    Leu Ser Ser Cys Pro Ser Gln Ala Leu Gln Leu Ala Gly Cys Leu Ser Gln Leu His Ser
                                                            90                                                        100
    Gly Leu Phe Leu Tyr Gln Gly Leu Leu Gln Ala Leu Glu Gly Ile Ser Pro Glu Leu Gly
                                                           110                                                        120
    Pro Thr Leu Asp Thr Leu Gln Leu Asp Val Ala Asp Phe Ala Thr Thr Ile Trp Gln Gln
                                                           130                                                        140
    Met Glu Glu Leu Gly Met Ala Pro Ala Leu Gln Pro Thr Gln Gly Ala Met Pro Ala Phe
                                                           150                                                        160
    Ala Ser Ala Phe Gln Arg Arg Ala Gly Gly Val Leu Val Ala Ser His Leu Gln Ser Phe
                                                           170
    Leu Glu Val Ser Tyr Arg Val Leu Arg His Leu Ala Gln Pro (AA)n
```

[Fig. 4]

```
  1                                                         10                                                         20
Met Thr Pro Leu Gly Pro Ala Ser Ser Leu Pro Gln Ser Phe Leu Leu Lys Cys Leu Glu Gln
                                                            30                                                         40
    Val Arg Lys Ile Gln Gly Asp Gly Ala Ala Leu Gln Glu Lys Leu Cys Ala Thr Tyr Lys
                                                            50                                                         60
    Leu Cys His Pro Glu Glu Leu Val Leu Leu Gly His Ser Leu Gly Ile Pro Trp Ala Pro
                                                            70                                                         80
    Leu Ser Ser Cys Pro Ser Gln Ala Leu Gln Leu Ala Gly Cys Leu Ser Gln Leu His Ser
                                                            90                                                        100
    Gly Leu Phe Leu Tyr Gln Gly Leu Leu Gln Ala Leu Glu Gly Ile Ser Pro Glu Leu Gly
                                                           110                                                        120
    Pro Thr Leu Asp Thr Leu Gln Leu Asp Val Ala Asp Phe Ala Thr Thr Ile Trp Gln Gln
                                                           130                                                        140
    Met Glu Glu Leu Gly Met Ala Pro Ala Leu Gln Pro Cys Gln Gly Ala Met Pro Ala Phe
                                                           150                                                        160
    Ala Ser Ala Phe Gln Arg Arg Ala Gly Gly Val Leu Val Ala Ser His Leu Gln Ser Phe
                                                           170
    Leu Glu Val Ser Tyr Arg Val Leu Arg His Leu Ala Gln Pro
```

[Fig. 5]

| | | Origin |
|---|---|---|
| 1- 29 | SD sequence | Synthetic DNA |
| 30- 560 | hG-CSF | Synthetic DNA |
| 561- 771 | Transcriptional Terminator (Toop) | Lambda phage DNA |
| 772-1586 | Rep of ori | pT7T319U |
| 1587-2610 | Kanamycin resistance gene | pACYC177 |
| 2611-2984 | par | pSC101 |
| 2985-3958 | cI857 and promoter | Lambda phage DNA |
| 3912-3917 | -35 (PR promoter) | Lambda phage DNA |
| 3935-3939 | -10 (PR promoter) | Lambda phage DNA |

[Fig. 6]

SEQUENCE LISTING

```
<160> NUMBER OF SEQ ID NOS: 19

<210> SEQ ID NO 1
<211> LENGTH: 174
<212> TYPE: PRT
<213> ORGANISM: Homo Sapiens

<400> SEQUENCE: 1

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 2
```

```
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 2
tgctctagaa aaaccaagg aggtaataaa ta                            32

<210> SEQ ID NO 3
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 3
ttactggacc ggatccgaat tctatta                                 27

<210> SEQ ID NO 4
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 4
aggaggtaat aaataatgtg tactccatta ggtcct                       36

<210> SEQ ID NO 5
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 5
gcaccagctc tgcaaccgtg tcaaggtgct atgccggca                    39

<210> SEQ ID NO 6
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 6
tgccggcata gcaccttgac acggttgcag agctggtgc                    39

<210> SEQ ID NO 7
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 7
ggatccgaat tctattaaca cggctgagcc agatg                        35

<210> SEQ ID NO 8
<211> LENGTH: 573
<212> TYPE: DNA
<213> ORGANISM: Homo Sapiens

<400> SEQUENCE: 8
tctagaaaaa accaaggagg taataaataa tgactccatt aggtcctgct tcttctctgc    60
```

```
cgcaaagctt tctgctgaaa tgtctggaac aggttcgtaa atccagggt gacggtgctg    120 cactgcaaga aaaactgtgc gctacttaca aactgtgcca tccggaagag ctggtactgc    180
tgggtcattc tcttggtatc ccgtgggctc cgctgtcttc ttgtccatct caagctcttc    240
agctggctgg ttgtctgtct caactgcatt ctggtctgtt cctgtatcag ggtcttctgc    300
aagctctgga aggtatctct ccggaactgg gtccgactct ggacactctg cagctagatg    360
tagctgactt tgctactact atttggcaac agatggaaga gctcggtatg caccagctc    420 tgcaaccgac tcaaggtgct atgccggcat cgcttctgc attccagcgt cgtgcaggag    480
gtgtactggt tgcttctcat ctgcaatctt tcctggaagt atcttaccgt gttctgcgtc    540
atctggctca gccgtaatag aattcggatc ccg                                 573

<210> SEQ ID NO 9
<211> LENGTH: 573
<212> TYPE: DNA
<213> ORGANISM: Homo Sapiens

<400> SEQUENCE: 9
cgggatccga attctattac ggctgagcca gatgacgcag aacacggtaa gatacttcca    60
ggaaagattg cagatgagaa gcaaccagta cacctcctgc acgacgctgg aatgcagaag   120
cgaatgccgg catagcacct tgagtcggtt gcagagctgg tgccataccg agctcttcca   180
tctgttgcca aatagtagta gcaaagtcag ctacatctag ctgcagagtg tccagagtcg   240
gacccagttc cggagagata ccttccagag cttgcagaag accctgatac aggaacagac   300
cagaatgcag ttgagacaga caaccagcca gctgaagagc ttgagatgga caagaagaca   360
gcggagccca cgggatacca agagaatgac ccagcagtac cagctcttcc ggatggcaca   420
gtttgtaagt agcgcacagt ttttcttgca gtgcagcacc gtcaccctgg attttacgaa   480
cctgttccag acatttcagc agaaagcttt gcggcagaga agaagcagga cctaatggag   540
tcattattta ttacctcctt ggttttttct aga                                 573

<210> SEQ ID NO 10
<211> LENGTH: 175
<212> TYPE: PRT
<213> ORGANISM: Homo Sapiens
<220> FEATURE:
<221> NAME/KEY: mat_peptide
<222> LOCATION: (2)..(2)

<400> SEQUENCE: 10

Met Thr Pro Leu Gly Pro Ala Ser Ser Leu Pro Gln Ser Phe Leu Leu
 -1  1               5                  10                  15

Lys Cys Leu Glu Gln Val Arg Lys Ile Gln Gly Asp Gly Ala Ala Leu
             20                  25                  30

Gln Glu Lys Leu Cys Ala Thr Tyr Lys Leu Cys His Pro Glu Glu Leu
         35                  40                  45

Val Leu Leu Gly His Ser Leu Gly Ile Pro Trp Ala Pro Leu Ser Ser
     50                  55                  60

Cys Pro Ser Gln Ala Leu Gln Leu Ala Gly Cys Leu Ser Gln Leu His
 65                  70                  75

Ser Gly Leu Phe Leu Tyr Gln Gly Leu Leu Gln Ala Leu Glu Gly Ile
 80                  85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
            115                 120                 125
```

```
Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
    145                 150                 155

Phe Leu Glu Val Ser Tyr Arg Val Leu Arg His Leu Ala Gln Pro
160                 165                 170

<210> SEQ ID NO 11
<211> LENGTH: 187
<212> TYPE: PRT
<213> ORGANISM: Homo Sapiens
<220> FEATURE:
<221> NAME/KEY: MISC_FEATURE
<222> LOCATION: (1)..(12)
<223> OTHER INFORMATION: Xaa can be any amino acid and includes at least
      one cysteine; any 2 to 12 of the amino acids at positions 1-12 may
      be absent
<220> FEATURE:
<221> NAME/KEY: mat_peptide
<222> LOCATION: (2)..(187)

<400> SEQUENCE: 11

Met Xaa Xaa Xaa Xaa Xaa Xaa Xaa Xaa Xaa Xaa Xaa Thr Pro Leu
 -1   1               5                  10                 15

Gly Pro Ala Ser Ser Leu Pro Gln Ser Phe Leu Leu Lys Cys Leu Glu
             20                  25                  30

Gln Val Arg Lys Ile Gln Gly Asp Gly Ala Ala Leu Gln Glu Lys Leu
            35                  40                  45

Cys Ala Thr Tyr Lys Leu Cys His Pro Glu Glu Leu Val Leu Leu Gly
            50                  55                  60

His Ser Leu Gly Ile Pro Trp Ala Pro Leu Ser Ser Cys Pro Ser Gln
 65                  70                  75

Ala Leu Gln Leu Ala Gly Cys Leu Ser Gln Leu His Ser Gly Leu Phe
 80                  85                  90                  95

Leu Tyr Gln Gly Leu Leu Gln Ala Leu Glu Gly Ile Ser Pro Glu Leu
                100                 105                 110

Gly Pro Thr Leu Asp Thr Leu Gln Leu Asp Val Ala Asp Phe Ala Thr
            115                 120                 125

Thr Ile Trp Gln Gln Met Glu Glu Leu Gly Met Ala Pro Ala Leu Gln
            130                 135                 140

Pro Thr Gln Gly Ala Met Pro Ala Phe Ala Ser Ala Phe Gln Arg Arg
            145                 150                 155

Ala Gly Gly Val Leu Val Ala Ser His Leu Gln Ser Phe Leu Glu Val
160                 165                 170                 175

Ser Tyr Arg Val Leu Arg His Leu Ala Gln Pro
                180                 185

<210> SEQ ID NO 12
<211> LENGTH: 187
<212> TYPE: PRT
<213> ORGANISM: Homo Sapiens
<220> FEATURE:
<221> NAME/KEY: mat_peptide
<222> LOCATION: (2)..(187)
<220> FEATURE:
<221> NAME/KEY: MISC_FEATURE
<222> LOCATION: (175)..(186)
<223> OTHER INFORMATION: Xaa represents any amino acid and includes at
      least one cysteine; any 2-12 of the amino acids at positions
      175-186 may be absent

<400> SEQUENCE: 12
```

```
Met Thr Pro Leu Gly Pro Ala Ser Ser Leu Pro Gln Ser Phe Leu Leu
 -1   1               5                  10                  15

Lys Cys Leu Glu Gln Val Arg Lys Ile Gln Gly Asp Gly Ala Ala Leu
              20                  25                  30

Gln Glu Lys Leu Cys Ala Thr Tyr Lys Leu Cys His Pro Glu Glu Leu
              35                  40                  45

Val Leu Leu Gly His Ser Leu Gly Ile Pro Trp Ala Pro Leu Ser Ser
              50                  55                  60

Cys Pro Ser Gln Ala Leu Gln Leu Ala Gly Cys Leu Ser Gln Leu His
 65                  70                  75

Ser Gly Leu Phe Leu Tyr Gln Gly Leu Leu Gln Ala Leu Glu Gly Ile
 80                  85                  90                  95

Ser Pro Glu Leu Gly Pro Thr Leu Asp Thr Leu Gln Leu Asp Val Ala
                 100                 105                 110

Asp Phe Ala Thr Thr Ile Trp Gln Gln Met Glu Glu Leu Gly Met Ala
                 115                 120                 125

Pro Ala Leu Gln Pro Thr Gln Gly Ala Met Pro Ala Phe Ala Ser Ala
                 130                 135                 140

Phe Gln Arg Arg Ala Gly Gly Val Leu Val Ala Ser His Leu Gln Ser
     145                 150                 155

Phe Leu Glu Val Ser Tyr Arg Val Leu Arg His Leu Ala Gln Pro Xaa
 160                 165                 170                 175

Xaa Xaa Xaa Xaa Xaa Xaa Xaa Xaa Xaa Xaa
                 180                 185

<210> SEQ ID NO 13
<211> LENGTH: 175
<212> TYPE: PRT
<213> ORGANISM: Homo Sapiens
<220> FEATURE:
<221> NAME/KEY: mat_peptide
<222> LOCATION: (2)..(2)

<400> SEQUENCE: 13

Met Thr Pro Leu Gly Pro Ala Ser Ser Leu Pro Gln Ser Phe Leu Leu
 -1   1               5                  10                  15

Lys Cys Leu Glu Gln Val Arg Lys Ile Gln Gly Asp Gly Ala Ala Leu
              20                  25                  30

Gln Glu Lys Leu Cys Ala Thr Tyr Lys Leu Cys His Pro Glu Glu Leu
              35                  40                  45

Val Leu Leu Gly His Ser Leu Gly Ile Pro Trp Ala Pro Leu Ser Ser
              50                  55                  60

Cys Pro Ser Gln Ala Leu Gln Leu Ala Gly Cys Leu Ser Gln Leu His
 65                  70                  75

Ser Gly Leu Phe Leu Tyr Gln Gly Leu Leu Gln Ala Leu Glu Gly Ile
 80                  85                  90                  95

Ser Pro Glu Leu Gly Pro Thr Leu Asp Thr Leu Gln Leu Asp Val Ala
                 100                 105                 110

Asp Phe Ala Thr Thr Ile Trp Gln Gln Met Glu Glu Leu Gly Met Ala
                 115                 120                 125

Pro Ala Leu Gln Pro Cys Gln Gly Ala Met Pro Ala Phe Ala Ser Ala
                 130                 135                 140

Phe Gln Arg Arg Ala Gly Gly Val Leu Val Ala Ser His Leu Gln Ser
     145                 150                 155

Phe Leu Glu Val Ser Tyr Arg Val Leu Arg His Leu Ala Gln Pro
 160                 165                 170
```

```
<210> SEQ ID NO 14
<211> LENGTH: 45
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (7)..(42)
<223> OTHER INFORMATION: NNN represents the DNA base sequence that
      encodes the corresponding amino acid, at least one of which is
      cysteine; any 4-36 of the corresponding amino acids at the n
      positions 7-42 may be absent

<400> SEQUENCE: 14
cagccgnnnn nnnnnnnnnn nnnnnnnnnn nnnnnnnnnn nntaa                     45

<210> SEQ ID NO 15
<211> LENGTH: 4
<212> TYPE: PRT
<213> ORGANISM: Artificial Sequence
<220> FEATURE:
<223> OTHER INFORMATION: Synthetic construct

<400> SEQUENCE: 15

Met Gly Cys Thr
1

<210> SEQ ID NO 16
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 16
gtaataaata atgggttgta ct                                              22

<210> SEQ ID NO 17
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(13)
<223> OTHER INFORMATION: Xaa can be any amino acid and includes at least
      one cysteine; 2-12 of the amino acids at positions 2-13 may be
      absent

<400> SEQUENCE: 17

Met Xaa Xaa Xaa Xaa Xaa Xaa Xaa Xaa Xaa Xaa Xaa Xaa Thr
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(14)
<223> OTHER INFORMATION: Xaa can be any amino acid and includes at least
      one cysteine; 2-12 of the amino acids at positions 3-18 may be
      absent

<400> SEQUENCE: 18

Gln Pro Xaa Xaa Xaa Xaa Xaa Xaa Xaa Xaa Xaa Xaa Xaa Xaa
```

```
1               5                    10

<210> SEQ ID NO 19
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(39)
<223> OTHER INFORMATION: NNN represents the DNA base sequence that
      encodes the corresponding amino acid, at least one of which is
      cysteine; 4-36 of the amino acids at the n positions 4-39 may be
      absent

<400> SEQUENCE: 19
atgnnnnnnn nnnnnnnnnn nnnnnnnnnn nnnnnnnnna ct                         42
```

HUMAN GRANULOCYTE-COLONY STIMULATING FACTOR ISOFORMS

TECHNICAL FIELD

The present invention relates to a novel human granulocyte colony stimulating factor isoform, by which in vivo lifetime of human granulocyte colony stimulating factor (rhG-CSF) is prolonged. More particularly, the present invention relates to a human granulocyte colony stimulating factor isoform, obtained from the covalent bonding of polyethylene glycol as a non-protein region to a human granulocyte colony stimulating factor isoform having cysteine added to the N-terminal or the C-terminal thereof.

BACKGROUND ART

Human granulocyte colony stimulating factor has the main biological function of stimulating specific leucocytes, known as neutrophilic granulocytes or neutrophils, to accomplish growth and development thereof in vivo (Welte et al., PNAS, 82, 1526-1530, 1985: Souza et al Science, 232, 61-65, 1986). Such neutrophilic granulocytes function to protect a biological species against infection with microorganisms, when they are discharged to blood flow.

The amino acid sequence of human granulocyte colony stimulating factor has been reported by Nagata et al. (Nature, 319, 415-418, 1986). Human granulocyte colony stimulating factor is a protein capable of forming a complex with a receptor thereof in a ratio of 2:2 via the dimerization of the receptor (Horan et al., Biochemistry, 35, 4886-96, 1996).

Aritomi et al. have shown the X-ray structure of the BN-BC domain complex of human granulocyte colony stimulating factor with a receptor thereof (Nature, 401, 713-717, 1999). It is reported by Aritomi et al. that amino acids of human granulocyte colony stimulating factor, which exist in contact region or adjacent region thereof when the receptor is bound to human granulocyte colony stimulating factor, include G4, P5, A6, S7, S8, L9, P10, Q11, S12, L15, K16, E19, Q20, L108, D109, D112, T115, T116, Q119, E122, E123 and L124.

Some isoforms of human granulocyte colony stimulating factor, obtained by protein engineering technique have been disclosed (U.S. Pat. No. 5,581,476, U.S. Pat. No. 5,214,132, U.S. Pat. No. 5,362,853, U.S. Pat. No. 4,904,584). Ridehall-Olsen et al., have reported that Lys40, Val48, Leu49 and Phe144, present in the amino acid sequence of human granulocyte colony stimulating factor, participate in the bonding with a receptor of human granulocyte colony stimulating factor. Additionally, Rayton et al. have reported that Glu46, Leu49 and Phe144 are in contact with an immunoglobulin-like domain (Ig-like domain) of a receptor of human granulocyte colony stimulating factor, while Lys40 and Val49 are away from the domain. Thus, it is not certain that Lys40 and Val49 are in contact with the receptor (J. biol. Chem., 2001, 276, 36779-36787). Further, Rayton et al., have demonstrated that Glu19 of human granulocyte colony stimulating factor interacts with Arg288 of a receptor thereof, thereby serving to transfer the signals of human granulocyte colony stimulating factor (J. Biol. Chem., 1999, 274, 17445-17451).

It has been suggested to introduce at least one additional sugar chain artificially into the human granulocyte colony stimulating factor protein by a genetic engineering method (U.S. Pat. No. 5,218,092). Such introduction of the sugar chain is performed by using a method of exchanging, deleting and adding amino acids in the amino acid sequence of a polypeptide.

Additionally, many studies including bonding of polyethylene to human granulocyte colony stimulating factor have been reported (Satake-Ishikawa et al. Cell Structure and Function, 17, 157-160, 1992; U.S. Pat. No. 5,824,778, U.S. Pat. No. 5,824,784, WO96/11953, WO95/21629, and WO94/20069).

In vivo removal of a polypeptide or a polymer thereof is made by removal (or clearance) and by receptor mediated degradation of protein in the kidney, spleen or liver. Such removal is accomplished by the action of a protease specific to a substrate or not. In general, in vivo protein removal depends on the size of protein (such a size that glomerular filtration can be prevented), the charge of a protein molecule, attachment of a sugar chain, protein receptor on the cell surface, or the like.

Particularly, protein removal in the kidney depends on the physical properties of a protein or a polymer thereof, such as size (molecular diameter), symmetry, shape/rigidity or charge, or the like.

Receptor mediated degradation of a protein is made when the protein loses its function upon the bonding with a receptor. At the initial time, leucocytes are insufficient, and bonding with a receptor on the surface of primordial hematopoietic stem cells results in differentiation and growth into leucocytes. However, once the number of leucocytes increases to reach a certain level, human granulocyte colony stimulating factor is removed by the receptor present on the surface of leucocytes in order to prevent excessive differentiation and growth caused by human granulocyte colony stimulating factor. The ratio of the primordial hematopoietic stem cells to the receptors of human granulocyte colony stimulating factor present on the surface of leucocytes is approximately 1:5.

Protein removal caused by the receptor present on the surface of leucocytes is executed by the introduction of a receptor-bound polypeptide into cells, and by lysosomal degradation of protein in the presence of proteases present in endosomes. Degradation of protein by bonding of a receptor to human granulocyte colony stimulating factor are described in detail by Saker and Roufenburger (Mol. Pharmacol., 2003, 63, 147-158) and Saker (Nature biotech. 2002, 20, 908-913).

To increase the half-life of a protein in blood, it is necessary to reduce protein removal in the kidney and degradation of the protein by bonding of a receptor. It is possible to reduce the protein removal in the kidney and to increase the half-life in vivo by bonding a polymer capable of increasing the apparent molecular size to the protein.

Moreover, adhesion of a polymer to a protein can interrupt proteases effectively and thus can prevent functions of non-specific proteases.

Among such polymers, polyethylene glycol (PEG) is one of the polymers widely used to prepare therapeutic protein products. Surface modification of a protein molecule caused by bonding of a protein drug to a synthetic polymer can increase the solubility of the drug to water or organic solvents. Accordingly, it is possible to increase the biocompatibility of the drug, to reduce the immunoreactivity, to improve the in vivo stability, and to retard clearance in the intestinal system, kidney, spleen or liver. Clearance of small protein molecules is made by filtering in the intestinal system or kidney. Hence, when a high-molecular weight PEG is bound to such small protein molecules, it is possible to prevent such clearance (Knauf, M. J. et al, J. Hiol. Chem. 263:15064, 1988). Introduction of a high-molecular weight polyethylene glycol (PEG) into a protein drug can increase the stability of the protein molecule in a solution. Additionally, it is possible to prevent adsorption of a non-specific protein by protecting the intrinsic surface characteristics of the protein effectively. In this regard, there has been an attempt to increase the in vivo half-life of a protein, to increase the solubility of a protein and to reduce the in vivo immunoreactivity by boding PEG to a biologically active peptide or protein. U.S. Pat. No. 4,179,337 reported the result of such attempts for the first time. Although bonding of PEG to a protein reduces many side effects due to the aforementioned advantages, the PEG-bound protein undesirably shows a significantly reduced in vivo activity because the active sites of the protein are blocked by PEG.

PEG, widely used up to date, is attached to the surface of protein by forming a covalent bond with at least one free lysine residue. Herein, if a site, which is present on the protein surface and is directly related to the activity of the protein, is bound to PEG, the activity of the protein decreases. Additionally, since the bonding between PEG and lysine residues occurs randomly, various kinds of PEG-bound protein conjugates are present in the form of a mixture, so that separation of a desired conjugate in a pure state becomes complicated and difficult. For example, EP 0401384 discloses a material and a method for producing polyethylene glycol-added G-CSF. EP0335423 discloses a modified polypeptide having an activity of human granulocyte colony stimulating factor. However, according to the prior art, the polyethylene glycol molecule cannot be bound to a predictable specific residue but bound to any reactive group present in the protein, such as a lysine residue, or the N-terminal in a non-specific manner, resulting in the formation of a non-homogeneous product. In order to bond a specific region of protein with PEG, U.S. Pat. No. 5,766,897 and WO00/42175 disclose a method of bonding human growth hormone with PEG, wherein PEG is allowed to react selectively with cysteine by using PEG-maleimide so as to prevent PEG from reacting with the active region of human growth hormone. It is required that a free cysteine residue that does not participate in disulfide bonding is present in human growth hormone to permit use of the above type of PEG. However, all of the four cysteine residues present in human growth hormone participate in disulfide bonding. Therefore, according to the prior art, pegylation is performed by using a human growth hormone derivative, into which a cysteine residue is artificially inserted. Additionally, U.S. Pat. No. 6,555,660 and U.S. Pat. No. 6,753,165 and US Laid-Open patent No. 2005/0058621 and KR2002-0079778 disclose mutation of cysteine at various positions in the amino acid sequence of human granulocyte colony stimulating factor.

Meanwhile, Bowen et al. have shown that molecular weight of polyethylene in polyethylene-modified human granulocyte colony stimulating factor is related to the lifetime of a drug. In an in vitro test, efficacy of a protein drug has an inverse relation with the molecular weight of polyethylene bound to the protein. However, in vivo activity increases as the molecular weight increases. It is thought that a polymer of a physiologically active protein shows a low affinity in receptor-mediated degradation, and thus shows an increased half life. Therefore, although such polymers of human granulocyte colony stimulating factor accomplish recovery of nutrophils in vivo, they show lower activity than the non-polymerized human granulocyte colony stimulating factor in terms of in vitro activity.

Recently, a modified human granulocyte colony stimulating factor that includes 20 kDa polyethylene glycol bound to the N-terminal has been developed and commercialized by Amgen, Inc. as Neulasta® (pegfilgrastim). The polyethylene glycol-polymerized human granulocyte colony stimulating factor has an increased half life, and thus can reduce administration frequency.

Particular examples of commercially available human granulocyte colony stimulating factor include *E. coli*-derived filgrastim (trade name: Gran and Neupogen), lenograstim (trade name: Neutroginand Granocyte) produced in animal cells, such as Chinese Hamster Ovary (CHO) cells, and *E. coli*-derived nartograstim (trade name: Neu-up), in which mutation occurs at the N-terminal regions in five amino acid sequences in order to increase the efficacy of human granulocyte colony stimulating factor protein.

DISCLOSURE OF INVENTION

Technical Problem

However, human granulocyte colony stimulating factor isoforms according to the prior art still have problems in that such amino acid sequence-modified human granulocyte colony stimulating factor isoforms have a low activity or insufficient half life in vivo, or non-homogeneous products are generated upon the bonding of PEG to human granulocyte colony stimulating factor.

Technical Solution

Therefore, the present invention has been made in view of the above-mentioned problems. It is an object of the present invention to provide a human granulocyte colony stimulating factor isoform having an excellent activity and a significantly increased half life by bonding polyethylene glycol to amino acid sequence-modified human granulocyte colony stimulating factor, wherein the amino acid sequence is modified by substitution with or addition of cysteine in a specific site in order to facilitate bonding polyethylene glycol to human granulocyte colony stimulating factor, and then the modified site is partially bound to polyethylene glycol. According to the prior art, human granulocyte colony stimulating factor isoforms have been generally produced by modifying the sequence in the polypeptide and performing pegylation at the position of a suitable amino acid in a specific site so as to increase the in vivo activity or lifetime. However, the inventors of the present invention have found that a novel isoform of human granulocyte colony stimulating factor, which shows an increased in vivo activity or lifetime compared to the isoforms according to the prior art, can be obtained by adding amino acids to both terminals of the polypeptide of human granulocyte colony stimulating factor and performing pegylation at the same addition sites. The present invention is based on this finding.

According to an aspect of the present invention, there is provided a human granulocyte colony stimulating factor isoform, which has at least one amino acid added before Thr of the N-terminal of human granulocyte colony stimulating factor represented by Sequence No. 1 or after Pro of the C-terminal thereof, wherein at least one of the amino acids added to human granulocyte colony stimulating factor is cysteine and at least one cysteine is bound to polyethylene glycol.

It is generally known to those skilled in the art that the N-terminal in Sequence No. 1 may include Met. In this case, the cysteine may be added between the Met and the threonine of the N-terminal. The above isoform is also included in the scope of the present invention.

More particularly, 1~12 amino acids may be added to each terminal of the sequence. Preferably, one cysteine is added. More preferably, the cysteine is 175C, added to the C-terminal.

According to a preferred embodiment of the present invention, polyethylene glycol is covalently bonded to the cysteine added to human granulocyte colony stimulating factor. Preferably, polyethylene glycol has a molecular weight of 20 kDa~40 kDa. More preferably, polyethylene glycol is branched.

According to another preferred embodiment of the present invention, at least one amino acid in human granulocyte colony stimulating factor is substituted with another amino acid before polyethylene glycol is bound to human granulocyte colony stimulating factor.

According to another aspect of the present invention, there is provided a pharmaceutical composition comprising the aforementioned human granulocyte colony stimulating factor isoform and a pharmaceutically acceptable carrier.

According to still another aspect of the present invention, there are provided genes encoding a protein of the aforementioned human granulocyte colony stimulating factor isoform having cysteine added to the N-terminal or C-terminal thereof.

According to yet another aspect of the present invention, there is provided an oligodeoxynucleotide used as a primer for modifying the amino acid sequence of human granulocyte colony stimulating factor into the aforementioned human granulocyte colony stimulating factor isoform. Preferably, the primer is the oligodeoxynucleotide represented by any one of Sequence Nos. 2~7.

Advantageous Effects

The human granulocyte colony stimulating factor isoform according to the present invention shows a significantly increased in vivo activity or lifetime, and thus can reduce administration frequency.

BRIEF DESCRIPTION OF THE DRAWINGS

The foregoing and other objects, features and advantages of the present invention will become more apparent from the following detailed description when taken in conjunction with the accompanying drawings in which:

FIG. 1 illustrates the genetic sequence (SEQ ID NOS:8-9) and protein sequence of human granulocyte colony stimulating factor (SEQ ID NO:10);

FIG. 2 illustrates the amino acid sequence of a human granulocyte colony stimulating factor isoform, amino acid-modified at the N-terminal site (SEQ ID NO:11);

FIG. 3 illustrates the amino acid sequence of a human granulocyte colony stimulating factor isoform, amino acid-modified at the C-terminal site (SEQ ID NO:12);

FIG. 4 illustrates the amino acid sequence of a human granulocyte colony stimulating factor isoform, amino acid-modified at the middle part of the polypeptide (SEQ ID NO:13);

BEST MODE FOR CARRYING OUT THE INVENTION

Reference will now be made in detail to the preferred embodiments of the present invention.

FIG. 1 illustrates the genetic sequence and protein sequence of human granulocyte colony stimulating factor. Amino acid sequence No. 1 is the same as the amino acid sequence represented in FIG. 1 with the exception of Met in −1 position.

FIG. 2 illustrates the amino acid sequence of a human granulocyte colony stimulating factor isoform, amino acid-modified at the N-terminal site. AA represents amino acids, and n is the number of amino acids. N is an integer ranging from 1 to 12. The amino acids include at least one cysteine.

FIG. 3 illustrates the amino acid sequence of a human granulocyte colony stimulating factor isoform, amino acid-modified at the C-terminal site. AA represents amino acids, and n is the number of amino acids. N is an integer ranging from 1 to 12. The amino acids include at least one cysteine.

FIG. 4 illustrates the amino acid sequence of a human granulocyte colony stimulating factor isoform, amino acid-modified at the part comprising a sugar chain. Herein, 133-threonine is substituted with cysteine, and polyethylene glycol is covalently bonded with the same cysteine. This is a known isoform according to the prior art (see Korean Laid-Open Patent No. 2002-0079778).

Figure 5:
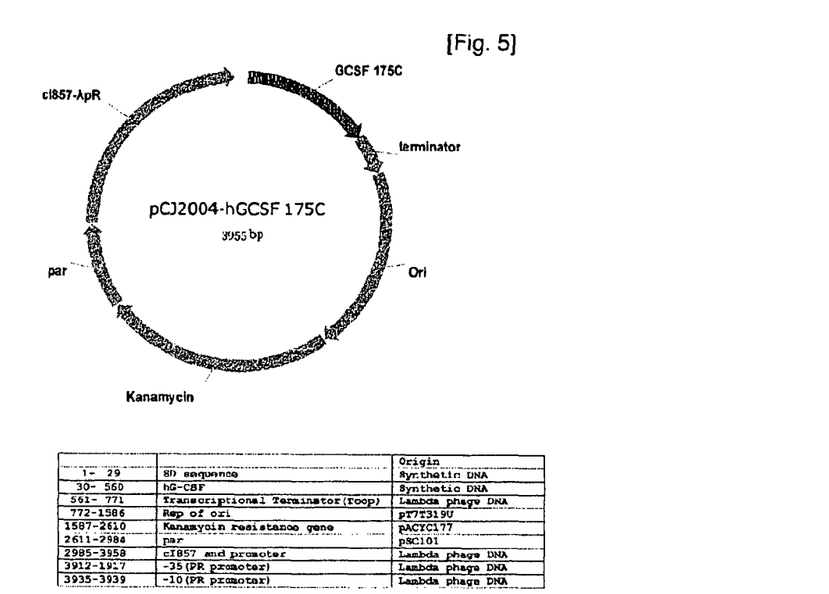
FIG. 5 illustrates the structure of a plasmid vector expressing a human granulocyte colony stimulating factor isoform.

FIG. 5 illustrates the structure of a plasmid vector expressing a human granulocyte colony stimulating factor isoform. As a promoter, PR of a bacteriophage lamda is used. To accomplish the expression in *E. coli*, widely used in laboratories, the plasmid vector includes cI 857 genes capable of inducing such expression in the plasmid vector.

Figure 6:
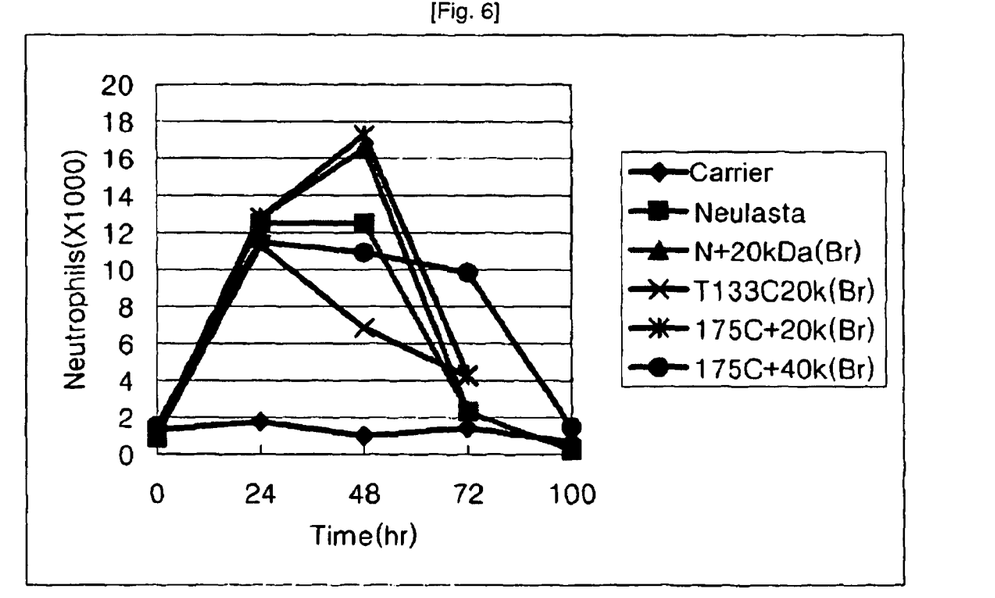
FIG. 6 is a graph showing the in vivo lifetime of human granulocyte colony stimulating factor isoforms in rats.

FIG. 6 is a graph showing the in vivo lifetime of human granulocyte colony stimulating factor isoforms in rats. PBS carrier is used as a control, and test samples include: T133C20 kDa(Br) (G-CSF isoform obtained by substituting 133-Thr with cysteine and covalently bonding branched PEG with 20 kDa to the same cysteine according to Korean Laid-Open Patent No. 2002-0079778); pegfilgrastim having 20 kDa PEG bound to the N-terminal; N+20 kDa(Br) (G-CSF isoform obtained by adding cysteine between the threonine and methionine of the N-terminal (−1C) of G-CSF and covalently bonding branched PEG with 20 kDa to the same cysteine); 175C+20 kDa(Br) (G-CSF isoform obtained by adding cysteine after 174-Pro of the C-terminal of G-CSF and covalently bonding branched PEG with 20 kDa to the same cysteine); and 175C+40 kDa(Br) (G-CSF isoform obtained by adding cysteine after 174-Pro of the C-terminal of G-CSF and covalently bonding branched PEG with 40 kDa to the same cysteine). Each isoform is diluted with PBS, and is administered to rats through the tail veins in a dose of 100 μg/kg 100/kg based on the body weight measured upon the administration day. Administration is carried out only once upon the test day.

The inventors of the present invention have studied the protein structure of human granulocyte colony stimulating factor and the effect of the amino acids forming human granulocyte colony stimulating factor upon the activity thereof. Reference has been made to the structure of human granulocyte colony stimulating factor, information about the effect of the amino acids forming human granulocyte colony stimulating factor upon the activity thereof, and to the results of GOR4 protein secondary structure prediction used to determine the effect of the modification of amino acids upon the protein structure.

As used herein, the term "human granulocyte colony stimulating factor isoforms" include analogs, variants, mutants, conjugates, or the like, which maintain the indigenous activity of human granulocyte colony stimulating factor, even though they experience modification of one amino acid residue into another amino acid residue in the original amino acid sequence of human granulocyte colony stimulating factor.

Three letter or single letter mnemonic codes for amino acids used herein are defined as follows according to biological standards:

Ala (A): alanine; Asx (B): asparagine or aspartic acid; Cys (C): cysteine; Asp (D): aspartic acid; Glu (E): glutamic acid; Phe (F): phenylalanine; Gly (G): glycine; His (H): histidine; Ile (I): isoleucine; Ls (K): lysine; Leu (L): leucine; Met (M): methionine; Asn (N): aspargine; Pro (P): proline; Gln (Q): glutamine; Arg (R): arginine; Ser (S): serine; Thr (T): threonine; Val (V): valine; Trp (w): tryptopane; Tyr (Y): tyrosine; Glx (Z): glutamine or glutamic acid.

As described herein, "(single letter for an amino acid) (amino acid position) (single letter for another amino acid)" means that the former amino acid in the corresponding amino acid position is substituted with the latter amino acid. For example, T133C means that threonine, the $133^{rd}$ amino acid in the sequence of natural human granulocyte colony stimulating factor, is substituted with cysteine.

Herein, the primer used to induce the modification of an amino acid at a specific site is represented by the expression (single letter for an amino acid) (amino acid position) (single letter for another amino acid) 1 or 2, wherein suffix 1 represents the primer for a single strand template progressing in the direction of 5'→3' in a double strand template, while suffix 2 represents the primer for a single strand template progressing in the direction of 3'→5'.

The human granulocyte colony stimulating factor genes obtained by the above process may be modified in the position at least one codon. As used herein, "modification" refers to a change in the amino acid sequence of human granulocyte colony stimulating factor caused by substitution or addition of at least one codon in the genes encoding human granulocyte colony stimulating factor. More particularly, such modification includes: addition of cysteine before threonine, the first amino acid in the amino acid sequence of human granulocyte colony stimulating factor; addition of cysteine after proline of the C-terminal of the same amino acid sequence; sequence modification in the middle of the polypeptide sequence in addition to the modification at the terminal sites; or the like.

For example, T133C means substitution of threonine, the $133^{rd}$ amino acid of natural human granulocyte colony stimulating factor, with cysteine. According to an embodiment of the present invention, a synthetic oligonucleotide including a codon that encodes modification of a target amino acid in human granulocyte colony stimulating factor is constructed. In general, an oligonucleotide with a length corresponding to about 27~36 nucleotides is used. Although a shorter oligonucleotide may be used, the oligonucleotide preferably has 12~15 nucleotides complementary to the template at both sides of the nucleotide encoding modification. Such oligonucleotides may be sufficiently hybridized with the template DNA. A synthetic oligonucleotide used for the amino acid modification according to the present invention is shown in the following Table 1. The oligonucleotide may be prepared by a method known to those skilled in the art.

According to a preferred embodiment of the present invention, DNA of human granulocyte colony stimulating factor isoform, one of whose amino acids is modified, is constructed. In this case, PCR is performed by using human granulocyte colony stimulating factor DNA (Table 1) as a template and a synthetic oligonucleotide encoding modification as a primer. If the double-strand template is separated in the heating step of PCR, a complementary primer is hybridized with each single strand template. DNA polymerase allows the nucleotides complementary to the template to be linked continuously thereto from —OH groups of the primer encoding modification along the direction of 5'→43'. As a result, the second strand includes the primer encoding modification, so that the resultant genes encode the target modification. The second strand functions as a template DNA during repeated replication steps, so that the genes encoding modification can be amplified continuously.

Hereinafter, modification in the middle of the polypeptide of human granulocyte colony stimulating factor will be explained in more detail with reference to T133C taken as an example. T133C refers to substitution of threonine, the $133^{rd}$ amino acid of natural human granulocyte colony stimulating factor, with cysteine. To obtain T133C, PCR is performed by using natural granulocyte colony stimulating factor DNA (FIG. 1) as a template and by introducing each of the primer pairs formed of N-term with T133C2 and T133C1 with C-term. By doing so, two DNA fragments, having a modified codon corresponding to cysteine that substitutes for threonine, the $133^{rd}$ amino acid, can be obtained. Then, PCR is further carried out by introducing the two DNA fragments and using primer pairs of N-term and C-term. In this manner, it is possible to obtain modified genes of human granulocyte colony stimulating factor isoform T133C, in which threonine is substituted with cysteine at the position of the $133^{rd}$ amino acid.

According to another example of the present invention, amino acid addition is made at the N-terminal or the C-terminal. Construction of human granulocyte colony stimulating factor having at least one modified amino acid can be performed at the N-terminal and the C-terminal. Such modification includes the sequence of Met-(AA)n-Thr- (SEQ ID NO:17) at the N-terminal (see FIG. 2) and the sequence of -Gin-Pro-(AA)n (SEQ ID NO:18) at the C-terminal (see FIG. 3). Herein, AA means any amino acid and particular examples thereof include an amino acid that has a low molecular weight and shows no specific function, such as glycine, serine or alanine. At least one AA includes cysteine. Suffix n means the number of amino acids and ranges from 1 to 12. At least about 12 amino acids are required for the in vivo recognition of the modified human granulocyte colony stimulating factor, to which amino acids are added, as a heterogeneous protein, followed by the production of an antibody. This is why the maximum number of amino acids is limited to 12.

Therefore, in order to construct human granulocyte colony stimulating factor genes having additional amino acids, the N-terminal has the amino acid sequence of Met-(AA)n-Thr- (SEQ ID NO:17) and includes the DNA base sequence of ATG-(NNN)n-ACT- (SEQ ID NO:19), while the C-terminal has the amino acid sequence of -Gln-Pro-(AA)n- (SEQ ID NO:18) and includes the DNA base sequence of -CAG-CCG-(NNN)n-TAA (SEQ ID NO:14). Herein, NNN represents the DNA base sequence that encodes the corresponding amino acid.

Then, human granulocyte colony stimulating factor genes having at least one modified amino acid are constructed by using the primer including the DNA base sequence obtained as described above and human granulocyte colony stimulating factor genes as shown in FIG. 1.

For example, if one glycine and one cysteine are added to the N-terminal, the amino acid sequence at the N-terminal may include the sequence of Met-(Gly-Cys-)Thr- (SEQ ID NO:15). The primer used herein may be designed to have the sequence of GTAATAAATA-ATG-(GGT-TGT-)ACT-(SEQ ID NO:16). Then, modified human granulocyte colony stimulating factor genes having the sequence of Met-(Gly-Cys-)Thr- (SEQ ID NO:15) may be constructed from the above primer, by using the template of human granulocyte colony stimulating factor genes as shown in FIG. 1 and the C-term primer as shown in Table 1.

The human granulocyte colony stimulating factor genes obtained as described above are further subjected to PCR by using N-term and C-term primers.

According to still another embodiment of the present invention, it is possible to add an amino acid to the N-terminal or C-terminal and to substitute at least one amino acid positioned in the middle of the polypeptide of human granulocyte colony stimulating factor with another amino acid, before polyethylene is bonded thereto. For example, −1C/T133C includes addition of cysteine to the N-terminal and substitution of the threonine, the $133^{rd}$ amino acid of the polypeptide of human granulocyte colony stimulating factor, with cysteine. To obtain −1C/T133C, PCR is performed by using preformed DNA of −1C human granulocyte colony stimulating factor isoform as a template and by introducing primer pairs of N-term with T122C2 and T133C1 with C-term. By doing so, two DNA fragments, having a modified codon corresponding to cysteine that substitutes for threonine, the $133^{rd}$ amino acid, can be obtained. Then, PCR is further carried out by introducing the two DNA fragments and using primer pairs of N-term and C-term. In this manner, it is possible to obtain modified genes of human granulocyte colony stimulating factor isoform −1C/T133C, in which threonine is substituted with cysteine at the position of the $133^{rd}$ amino acid and cysteine is added before the threonine of the N-terminal. Construction of isoforms at a position other than 133 may be performed by using the corresponding DNA primer in the same manner as −1C/T133C isoform.

Modification of amino acid in the middle of the polypeptide of the amino acid-added isoform including at least one cysteine at the N-terminal or the C-terminal can be performed at a site known to those skilled in the art. For example, methods of substituting at least one amino acid in the middle of the polypeptide of human granulocyte colony stimulating factor with another amino acid are disclosed in Korean Patent Publication No. 0248111 (N-terminal polyethylene glycol-bound G-CSF or analogues thereof, and preparation thereof), Korean Laid-Open Patent Nos. 2002-0007297 (G-CSF conjugates), 2002-0079778 (G-CSF conjugates) and 2004-0084884 (G-CSF conjugates), U.S. Pat. Nos. 5,214,132 (Polypeptide derivatives of human granulocyte colony stimulating factor) and 5,416,195 (Polypeptide derivatives of granulocyte colony stimulating factor), US Laid-Open Patent Nos. 2003-0158375 (G-CSF polypeptides and conjugates), 2004-0214287 and 2005-0058621. More particularly, according to U.S. Pat. No. 5,214,132, U.S. Pat. No. 5,416,195 and US2004-0214287, 1, 3, 4, 5 and 17-position amino acids of human granulocyte colony stimulating factor are substituted with Ala, Thr, Tyr, Arg and Ser, respectively, or the cysteine, 17-position amino acid, is substituted with alanine or serine.

The contents of the above patents and patent applications are herein incorporated by reference. Also, methods of producing human granulocyte colony stimulating factor isoforms, pegylation methods, or the like, as disclosed in the prior art are also herein incorporated by reference.

The DNA sequence that encodes the human granulocyte colony stimulating factor isoforms according to the present invention may be synthesized by the conventional method known to those in the art, for example, by using an automatic DNA synthesizer (available from Biosearch, Applied Biosystem™, etc.).

According to still another aspect of the present invention, there is provided a recombinant expression vector including the DNA sequence encoding the human granulocyte colony stimulating factor isoform and a host cell transformed or transfected with the above expression vector.

As used herein, the term "polypeptide" may be used interchangeably with "protein" or "physiologically active protein".

As used herein, the term "isoform" means a physiologically active protein, which has the main function of the original physiologically active protein but is modified with a genetic engineering means or others. Herein, the term "modification" refers to substitution, addition and loss in an amino acid sequence, and includes substitution with cysteine or addition of cysteine for carrying out bonding with polyethylene glycol. Further, such modification also includes a covalent bonding formed between cysteine and polyethylene glycol via a chemical reaction.

As used herein, the term "in vivo lifetime" is defined as follows: a physiologically active protein loses its function when it is administered to humans or animals, because the total amount and activity of the physiologically active protein decrease due to the protease-mediated removal and the removal in the kidney. Therefore, the term "in vivo lifetime" means the retention time of a protein during which the protein can perform its function in vivo, and is represented by the in vivo half life of the physiologically active protein.

As used herein, the term "vector" refers to a DNA molecule as a carrier capable of delivering foreign genes stably into a host cell. To be a useful vector, it is necessary for a vector to allow replication, to have a means, through which it can be introduced into a host cell, and to include a means for detecting itself. Additionally, the term "recombinant expression vector" refers to a cyclic DNA molecule formed by a vector linked operatively to foreign genes so that the foreign genes can be expressed in a host cell.

As a recombinant expression vector, a DNA vector having human granulocyte colony stimulating factor inserted thereto, may be produced. When constructing a recombinant expression vector, in order to increase the expression level of transfected genes in a host cell, the corresponding genes should be linked operatively to a transcription and translation expression regulatory sequence that functions in a selected host cell, as generally known in the art. Preferably, the expression regulatory sequence and the corresponding genes are included in a single expression vector that further includes a bacterial selection marker and a replication origin.

A suitable vector including not only the genes encoding human granulocyte colony stimulating factor isoforms but also the above elements (e.g. regulatory sequence) can be constructed by using basic recombinant DNA technique. In order to form a desired vector, individually separated DNA fragments should be linked to each other. Thus, each DNA fragment is cleaved first by using restriction enzymes, and then the DNA fragments are linked to each other considering a specific order and orientation.

DNA may be cleaved by using a specific restriction enzyme in a suitable buffer. In general, about 0.2–1 μg of a plasmid or DNA fragment is used in about 20 μl of a buffer solution along with about 1–2 units of the corresponding restriction enzyme. Suitable buffer, DNA concentration, reaction time and reaction temperature will be determined by the producer of the restriction enzyme. Generally, the reaction is carried out at 37° C. for about 1–2 hours. However, some enzymes require a higher temperature. After the reaction, enzymes and other impurities are removed by extracting the digestion solution with a mixture of phenol and chloroform. DNA may be precipitated with ethanol to recover it from aqueous layer. At this time, terminals of DNA fragments to be linked to each other should be compatible with each other in order to link DNA fragments so that a functional vector can be formed.

The cleaved DNA fragments are classified and selected on the size basis via electrophoresis. DNA electrophoresis may be performed through an agarose or polyacrylamide matrix. Selection of the matrix depends on the size of DNA to be separated. After the electrophoresis, DNA is extracted from the matrix via electroelution, or extracted directly from the matrix. When a low-melting agarose matrix is used, agarose should be melted before the extraction of DNA.

DNA fragments to be linked to each other should be added to a solution in an equimolar amount. The solution contains ATP, ligase buffer, and about 10 units ligase such as T4 ligase per 0.5 µg of DNA. To link DNA fragments to a vector, the vector should be cleaved by a suitable restriction enzyme first to form a linear vector. Such linear vector may be used after it is treated with alkali phosphatase or bovine intestinal hydrolase. Such treatment with hydrolase prevents the vector from self-ligation. The recombinant expression vector constructed as described above is used to perform transformation or transfection of a host cell.

Polynucleotides can be introduced into a host cell according to a known method disclosed in laboratory manuals such as [Davis et al., Basic Methods in Molecular biology (1986)] and [Sambrook, J., et al. (1989) "Molecular Cloning" A laboratory Manual $2^{nd}$ edition]. Preferred methods of introducing polynucleotides into a host cell include calcium chloride transformation, electroporation, or the like.

According to the present invention, host cells are incubated in a nutrition medium suitable for the production of polypeptides by using a known technique. For example, hose cells may be incubated in a laboratory or industrial fermenting instrument via small-scale or large-scale fermentation/shaking flask incubation with a suitable medium under the conditions permitting expression and/or secretion of polypeptides. Incubation is performed in a suitable nutrition medium containing a carbon source, a nitrogen source and inorganic salts by using a known technique. The medium is generally known to those skilled in the art and is commercially available. Otherwise, a medium prepared directly in a laboratory may be used. If polypeptides are secreted directly to the nutrition medium, the polypeptides can be separated directly from the medium. If polypeptides are not secreted to the nutrition medium, they can be separated from the cell lysate.

Separation of polypeptides can be performed in a conventional manner. For example, polypeptides can be separated from the medium by a conventional method including centrifugal separation, filtration, extraction, spray drying, evaporation or precipitation. Further, purification of polypeptides can be performed by various methods known to those skilled in the art, including chromatography (e.g. ion exchange chromatography, affinity chromatography, hydrophobic chromatography or size exclusion chromatography), electrophoresis, fractional solubility separation (e.g. ammonium sulfate precipitation), SDS-PAGE or extraction.

Then, the human granulocyte colony stimulating factor isoform purified as described above is subjected to pegylation in the manner as described hereinafter.

Suitable "non-protein segments" used for the pegylation according to the present invention include polyethylene glycol, and branched polyethylene glycol is preferred. Other examples of such non-protein segments include, but are not limited to: at least one material selected from the group consisting of water soluble polymers such as polypropylene glycol (PPG), polyoxyethylene (POE), polytrimethylene glycol, polylacatic acid and derivatives thereof, polyacrylic acid and derivatives thereof, poly(amino acid), poly(vinyl alcohol), polyurethane, polyphosphazenes, poly(L-lysine), polyalkylene oxide (PAO), polysaccharide, or the like, and non-immune polymers such as dextran, polyvinyl pyrrolidone, polyvinyl alcohol (PVA), polyacryl amide, or the like. The biocompatible polymer used in the preparation of the polymer derivatives according to the present invention preferably has a molecular weight of about 2,000~100,000, more preferably 20,000~40,000.

In order to form a bond between a biocompatible polymer and G-CSF via the thiol group of G-CSF, the biocompatible polymer should be activated. For this purpose, the biocompatible polymer may be bonded with a reactive functional group. The term "reactive polymer group" means a group or a moiety capable of activating a biocompatible polymer so that it can be bonded with a biologically active material. To form a bond between a biocompatible polymer and a biologically active material, one of the terminal groups of the biocompatible polymer is converted into a reactive functional group. This process is referred to as "activation". For example, to form a bond between poly(alkylene oxide) and a biologically active protein, one of the hydroxyl terminal groups may be converted into a reactive group, such as carbonate. As a result, activated poly(alkylene oxide) can be obtained.

The reactive group that may be used to activate a biocompatible non-protein segment polymer according to the present invention is selected from the group consisting of maleimide, acetamide, pentenoic amide, butenoic amide, isocyanate, isothiocyanate, cyan uric acid chloride, 1,4-benzoquinone, disulfide, or the like.

Bonding PEG to a protein via a thiol group of the protein can be performed by a method generally known to those skilled in the art.

For example, PEG-maleimide is used to allow thiol groups to be bound to activated double bonds via Michael reaction [Ishii et al., Biophys J. 1986, 50:75-80]. Additionally, as generally known to those in the field of protein chemistry, PEG-iodoacetamide reagent may be used. The latter method is advantageous in that a stable PEG-bound cysteine derivative, i.e. carboxymethyl cysteine, can be obtained by a strong acidic hydrolysis, wherein the derivative can be identified and determined by standard amino acid analysis [Gard F R N. Carboxymethylation, Method Enzymol 1972; B25: 424-49]. In addition to the above methods, a method of producing a stable symmetric disulfide by using PEG-ortho-pyrimidyl-disulfide (Woghiren et al. Bioconjugate Chem 1993, 50:75-80); a method of reacting an activated PEG, i.e. sulfosuccinimidyl 4-(N-maleimidomethyl)cyclohexane-1-carboxylate activated-PEG with thiol group of cysteine to form a covalent bond [U.S. Pat. No. 5,166,322]; a method of reacting an activated PEG, i.e. maleimido-6-aminocaproylester-activated PEG 4000 with the IL-2 mutant having a cysteine substituent at a specific site so as to be conjugated with a cysteine residue [U.S. Pat. No. 5,206,344]; and a method of modifying thiol groups of a protein by using gamma-maleimidobutyric acid and beta-maleimidopropionic acid [Rich et al., J. Med. Chem. 18, 1004, 1975] may be used.

The pegylation method in the following examples were performed by using mPEG20,000-maleimide, branched mPEG20,000-maleimide and branched mPEG40,000 available from NOF in a molar ratio of 20:1 to human granulocyte colony stimulating factor. The pegylation reaction is performed in 0.1M phosphate buffer (pH 7-8) at room temperature for 2 hours with stirring.

Pharmaceutically acceptable carriers, excipients or stabilizers must be non-toxic to the subjects and be compatible with other constituents of the pharmaceutical preparation under the corresponding administration dose and concentration. For example, the pharmaceutical preparation should not contain any materials known to be harmful to polypeptides, such as oxidants or other materials.

Suitable carriers include: buffers such as phosphoric acid, citric acid and other organic acids; antioxidants including ascorbic acid; low-molecular weight polypeptides; proteins such as blood plasma albumin, gelatin and immunoglobulin; hydrophilic polymers such as polyvinyl pyrrolidone; amino acids such as glycine, glutamin, arginine, or lysine; monosaccharides, disaccharides or other carbohydrates including glucose, mannose or dextrin; chelate factors such as EDTA; metal ions such as zinc, cobalt or copper; sugar alcohols such as mannitol or sorbitol; salt-forming counterions such as sodium; and/or non-ionic surfactants such as Tween, Pluronic or polyethylene glycol (PEG).

A sugar chain-bound human granulocyte colony stimulating factor isoform should be sterilized before it is administered for the purpose of treatment. Such sterilization may be accomplished easily by way of filtering through a sterilized filtration membrane.

In general, a therapeutic sugar chain-bound human granulocyte colony stimulating factor isoform composition is stored in a container equipped with a sterilized access port, for example, an intravenous injection bag or vial having a septum through which a subcutaneous injection needle can pass.

The human granulocyte colony stimulating factor isoform according to the present invention may be administered directly to animals by suitable routes including parenteral administration routes, locally or systematically. A particular administration route will be determined by the history of a patient, including side effects recognized or expected upon the administration of human granulocyte colony stimulating factor isoform. Particular parenteral administration routes include subcutaneous, intramuscular, intravenous, intraarterial and intraperitoneal routes. Most preferably, administration is carried out by continuous infusion (e.g. mini-pump such as an osmotic pump) or injection, for example, intravenous injection or subcutaneous injection. A preferred administration route for human granulocyte colony stimulating factor isoform is subcutaneous administration.

The human granulocyte colony stimulating factor isoform according to the present invention may be administered to a patient in a therapeutically effective amount. The term "therapeutically effective amount" refers to the amount sufficient to obtain a desired treating effect by using a given administration mode under a given condition. The therapeutic composition of human granulocyte colony stimulating factor should be formulated and administered conformed to the preferred medical practice, under the consideration of the particular condition to be treated, clinical conditions of an individual patient (particularly, side effects upon the single administration of human granulocyte colony stimulating factor), delivery sites of the composition of the human granulocyte colony stimulating factor isoform, administration modes, administration schedules and other factors generally known to those skilled in the art. The therapeutically effective amount of the human granulocyte colony stimulating factor isoform is determined considering the above factors. In general, daily dose of the human granulocyte colony stimulating factor isoform according to the present invention ranges from about 1 μug/kg to 100 μg/kg.

Reference will now be made in detail to the preferred embodiments of the present invention. It is to be understood that the following examples are illustrative only, and the scope of the present invention is not limited thereto.

EXAMPLE 1

Construction of Human Granulocyte Colony Stimulating Factor Isoforms

To construct isoforms of natural human granulocyte colony stimulating factor, human granulocyte colony stimulating factor genes were synthesized as a template. The genes synthesized in this example have base sequences as shown in the following Table 1, and DNA sequence and amino acid sequence of human granulocyte colony stimulating factor, used as a template, are shown in FIG. 1. In Table 1, N-term~175C correspond to Sequence Nos. 2~7, respectively.

TABLE 1

| | |
|---|---|
| N-Term | 5'TGCTCTAGAAAAAACCAAGGAGGTAATAAATA3'<br>(SEQ ID NO: 2) |
| C-Term | 5'TTACTGGACCGGATCCGAATTCTATTA3'<br>(SEQ ID NO: 3) |
| -1C | 5'AGGAGGTAATAAATAATGTGTACTCCATTAGGTCCT3'<br>(SEQ ID NO: 4) |
| T133C1 | 5'GCACCAGCTCTGCAACCGTGTCAAGGTGCTATGCCGGCA3'<br>(SEQ ID NO: 5) |
| T133C2 | 5'TGCCGGCATAGCACCTTGACACGGTTGCAGAGCTGGTGC3'<br>(SEQ ID NO: 6) |
| 175C | 5'GGATCCGAATTCTATTAACACGGCTGAGCCAGATG3'<br>(SEQ ID NO: 7) |

1. Construction of −1C Human Granulocyte Colony Stimulating Factor Isoform

PCR was performed to construct −1C isoform by using DNA of natural human granulocyte colony stimulating factor as a template and primer pairs formed of −1C primer and C-term primer. The amplified DNA fragment was further subjected to PCR by using N-term primer and C-term primer so that restriction enzyme cleavage sites (Xba I and BamH I) could be introduced, and then was introduced into an expression vector. By doing so, it was possible to obtain genes of a human granulocyte colony stimulating factor isoform having cysteine added before threonine of the N-terminal.

The amino acid sequence of the N-terminal was methionine-cysteine-threonine-proline-leucine-glycine.

2. Construction of T133C Human Granulocyte Colony Stimulating Factor Isoform

T133C was constructed in order to provide a control as a known isoform or to realize amino acid modification in the middle of the polypeptide of human granulocyte colony stimulating factor. T133C, having cysteine substituting for threoninine, the 133$^{rd}$ amino acid of natural human granulocyte colony stimulating factor, was obtained by carrying out PCR using DNA of natural human granulocyte colony stimulating factor as a template and primer pairs formed of N-term primer with T133C2 and T133C1 with C-term primer. As a result, it was possible to obtain two DNA fragments modified with a codon corresponding to cysteine substituting for threonine, the 133$^{rd}$ amino acid. The two DNA fragments were further subjected to PCR by using primer pairs formed of N-term primer and C-term primer to obtain modified genes of T133C, a human granulocyte colony stimulating factor isoform having cysteine substituting for threonine in the position of the 133$^{rd}$ amino acid. Introduction into an expression vector was performed in the same manner as described in the above 'Construction of −1C Human Granulocyte Colony Stimulating Factor Isoform'.

3. Construction of −1C/T133C Human Granulocyte Colony Stimulating Factor Isoform −1C/T133C was constructed in order to realize amino acid addition to the N-terminal and amino acid modification in the middle of the polypeptide of human granulocyte colony stimulating factor. To construct −1C/T133C, threoninine, the $133^{rd}$ amino acid of the preformed −1C human granulocyte colony stimulating factor isoform, was substituted with cysteine. For this, PCR was performed by using DNA of the preformed −1C human granulocyte colony stimulating factor isoform as a template and primer pairs formed of N-term primer with T133C2 and T133C1 with C-term primer. As a result, it was possible to obtain two DNA fragments modified with a codon corresponding to cysteine substituting for threonine, the $133^{rd}$ amino acid. The two DNA fragments were further subjected to PCR by using primer pairs formed of N-term primer and C-term primer to obtain modified genes of −1C/T133C, a human granulocyte colony stimulating factor isoform having cysteine substituting for threonine in the position of the $133^{rd}$ amino acid. Introduction into an expression vector was performed in the same manner as described in the above 'Construction of −1C Human Granulocyte Colony Stimulating Factor Isoform'.

4. Construction of 175C Human Granulocyte Colony Stimulating Factor Isoform

To construct 175C, PCR was performed by using DNA of natural human granulocyte colony stimulating factor as a template and primer pairs formed of N-term primer and 175C primer. The amplified DNA fragment was further subjected to PCR by using N-term primer and C-term primer so that restriction enzyme cleavage sites (Xba I and BamH I) could be introduced, and then was introduced into an expression vector. By doing so, it was possible to obtain genes of a human granulocyte colony stimulating factor isoform having cysteine added to the N-terminal. Introduction into the expression vector was performed in the same manner as described in the above 'Construction of −1C Human Granulocyte Colony Stimulating Factor Isoform'.

The amino acid sequence of the C-terminal was -alanine-glutamine-proline-cysteine.

5. Construction of 175C/T133C Human Granulocyte Colony Stimulating Factor Isoform To construct 175C/T133C, threoninine, the $133^{rd}$ amino acid of the preformed −1C human granulocyte colony stimulating factor isoform, was substituted with cysteine. For this, PCR was performed by using DNA of the preformed 175O human granulocyte colony stimulating factor isoform as a template and primer pairs formed of N-term primer with T133C2 and T133C1 with C-term primer. As a result, it was possible to obtain two DNA fragments modified with a codon corresponding to cysteine substituting for threonine, the $133^{rd}$ amino acid. The two DNA fragments were further subjected to PCR by using primer pairs formed of N-term primer and C-term primer to obtain modified genes of 175C/T133C, a human granulocyte colony stimulating factor isoform having cysteine substituting for threonine in the position of the $133^{rd}$ amino acid. Introduction into an expression vector was performed in the same manner as described in the above 'Construction of −1C Human Granulocyte Colony Stimulating Factor Isoform'.

The genes of the human granulocyte colony stimulating factor isoforms constructed as described above were introduced into an expression vector so as to be expressed by a lamda PR promoter. Constitutional elements of the expression vector are shown in the following Table 2.

TABLE 2

| | Origin |
|---|---|
| PR promoter | NEB Ltd. lamda DNA#301-18 |
| Self-replication machine | pT7T319U |
| Antibiotic marker (Kanamycin) | pACYC177 |
| Par | pSC101 |
| cI 857 represor | NEB Ltd. lamda DNA#301-18 |
| SD sequence | Synthesized DNA |
| Transcription terminating site | NEB Ltd. lamda DNA#301-18(toop) |

EXAMPLE 2

Expression and Purification of Human Granulocyte Colony Stimulating Factor Isoforms Transformation of plasmid vectors containing genes of human granulocyte colony stimulating factor isoforms into *E. coli* was performed to construct strains producing human granulocyte colony stimulating factor proteins.

To perform the transformation, the calcium chloride method generally known to those skilled in the art was used. Herein, *E. coli* used as a host cell was currently available *E. coli* (HB101, NM strain series, etc.).

The transformed *E. coli* was inoculated into 5 ml of a Luria Broth (LB) medium in a 15 ml tube, and was incubated (cultured) overnight in an incubator at 30° C. The seed cells culture was inoculated into a 500 ml of Luria Broth (LB) medium in a 3,000 ml triangular flask and was incubated at 30° C. When the absorbance at 600 nm reached 0.8-1.2, the incubator was heated to 42° C. and the cells were further incubated for 4 hours to induce the expression of human granulocyte colony stimulating factor isoforms.

After the completion of the culture, the culture solution was subjected to centrifugal separation to collect the cells, and the cells were washed with distilled water. The washed cells were lysed in a microfluidizer (available from Microfluidics Co.) under 12,000 psi four times, and inclusion bodies were recovered via centrifugal separation, followed by washing three times with distilled water.

The inclusion bodies were thoroughly suspended and dissolved in 10 ml of 8M urea, 50 mM glycine (pH 11.0) at room temperature for at least 5 hours, and then the suspension was subjected to centrifugal separation at 10,000 rpm for 30 minutes. The supernatant was collected to obtain a solution of human granulocyte colony stimulating factor isoform protein. To the protein solution, glycine and distilled water were added to control the glycine concentration and the urea concentration to 50 mM and 2M, respectively. The resultant protein solution was titrated to pH 9.0 and was subjected to protein refolding overnight at 4° C.

After the completion of the protein refolding, the solution was adjusted to pH 4.0, diluted with distilled water by three times or more, and was loaded to a column packed with 10 ml of CM Sepharose™ Fast Flow (available from GE Healthcare), which have been previously equilibrated by using 2 mM HCl in an amount of at least three times of the column volume. After the completion of the loading, the column was equilibrated by using 2 mM HCl in an amount of at least three times of the column volume, and washed by using 50 mM acetate sodium chloride buffer (pH 5.4) in an amount of at least three times of the column volume. Then, human granulocyte colony stimulating factor isoforms were eluted by using 50 mM acetate sodium chloride buffer (pH 5.4) containing 35 mM sodium chloride in an amount of at least twelve times of the column volume and were divided into 5 ml fractions. The fractions were collected after the HPLC analysis.

The human granulocyte colony stimulating factor isoforms, purified by CM Sepharose™ Fast Flow, were concentrated by using a Centricon® Plus-80 filter unit with a molecular weight of 10,000 Da at 3000 rpm for 25 minutes to obtain protein concentrate having a final protein concentration of about 5 mg/ml.

The concentrated protein was loaded to a column packed with 300 ml of Sephacryl™ S-100 (GE Healthcare), which have been previously equilibrated by using 10 mM acetate sodium chloride buffer (pH 5.4) in an amount of at least three times of the column volume. The buffer solution was eluted at a rate of 1 ml/min to remove multimers of the human granulocyte colony stimulating factor isoforms contained in the protein solution and to separate purified monomers, which, in turn, was used in the subsequent polyethylene glycol addition reaction.

EXAMPLE 3

Bonding of Polyethylene Glycol to Human Granulocyte Colony Stimulating Factor Isoforms 1. Preparation of Branched mPEG (20,000)-Maleimide-G-CSF Isoform 10 mg of each of the human granulocyte stimulating factor isoforms according to Example 2 was introduced into 0.1M phosphate buffer (pH 7.0-8.0) and 200 mg of branched mPEG (20,000)-maleimide (available from NOF) was added thereto. Reaction was performed at room temperature for 2 hours with stirring. The reaction mixture was quenched by reducing pH to 3.0 with 1N HCl solution.

2. Preparation of Branched mPEG (40,000)-maleimide-G-CSF Isoform 10 mg of each of the human granulocyte stimulating factor isoforms according to Example 2 was introduced into 0.1M phosphate buffer (pH 7.0-8.0) and 400 mg of branched mPEG (40,000)-maleimide (available from NOF) was added thereto. Reaction was performed at room temperature for 2 hours with stirring. The reaction mixture was quenched by reducing pH to 3.0 with 1N HCl solution.

EXAMPLE 4

Purification of Polymer of Human Granulocyte ColonyStimulating Factor Isoform with Polyethylene Glycol The PEG-G-CSF polymer obtained from Example 3 was purified as follows.

1. CM Sepharose™ Fast Flow Chromatography

After the completion of the reaction, each mPEG-G-CSF polymer was titrated to pH 3.0, diluted with distilled water by at least 10 times, and loaded to a column packed with 10 ml of CM Sepharose™ Fast Flow, which have been previously equilibrated by using 2 mM HCl in an amount of at least three times of the column volume. After the loading, the column was equilibrated by using 2 mM HCl in an amount of at least three times of the column volume, and washed by using 50 mM acetate sodium chloride buffer (pH 5.0) in an amount of three times of the column volume. In the cases of mPEG (20,000)-maleimide-G-CSF isoform and branched mPEG (20,000)-maleimide-G-CSF isoform, mPEG-G-CSF polymers were eluted by using 50 mM acetate sodium chloride buffer (pH 5.4) containing 40 mM sodium chloride in an amount at least twelve times of the column volume. In the case of Branched mPEG (40,000)-maleimide-G-CSF isoform, mPEG-G-CSF polymer was eluted by using 50 mM acetate sodium chloride buffer (pH 5.4) containing 20 mM sodium chloride in an amount at least twelve times of the column volume. The eluted solution was fractionated into a 5 ml fraction and each fraction was collection after the HPLC analysis.

2. Gel Permeation Chromatography

The mPEG-G-CSF polymers, purified by CM Sepharose™ Fast Flow, were concentrated by using a Centricon® Plus-80 filter unit with a molecular weight of 10,000 Da at 3000 rpm for 25 minutes to obtain protein concentrate having a final protein concentration of about 5 mg/ml.

The concentrated protein was loaded to a column packed with 300 ml of Sephacryl™ S-100, which have been previously equilibrated by using 10 mM acetate sodium chloride buffer (pH 5.4) in an amount of at least three times of the column volume. The buffer solution was eluted at a rate of 1 ml/min to remove mPEG-G-CSF polymers contained in the protein solution. Proteins were serially eluted in the order of G-CSF multimer, PEG-G-CSF, G-CSF dimer and G-CSF monomer.

EXAMPLE 5

Evaluation of Activity and in vivo lifetime of mPEG-G-CSF Polymers in Rats

The mPEG-G-CSF polymers prepared and purified according to Example 4 were evaluated for the activity and in vivo lifetime by using 8-week aged rats (SD rats, male, five rats per test sample). The test samples include: PBS carrier as a carrier; G-CSF T133C20 kDa(Br) prepared and purified according to Examples 1 to 4 (G-CSF isoform obtained by substituting 133-Thr with cysteine and covalently bonding branched PEG with 20 kDa to the same cysteine according to Korean Laid-Open Patent No. 2002-0079778); pegfilgrastim having 20 kDa PEG bound to the N-terminal; and the isoforms according to the present invention, prepared and purified according to Examples 1 to 4, i.e. N+20 kDa(Br), (G-CSF isoform obtained by adding cysteine between the threonine and methionine of the N-terminal (−1C) of G-CSF and covalently bonding branched PEG with 20 kDa to the same cysteine); 175C+20 kDa(Br) (G-CSF isoform obtained by adding cysteine after 174-Pro of the C-terminal of G-CSF and covalently bonding branched PEG with 20 kDa to the same cysteine); and 175C+40 kDa(Br) (G-CSF isoform obtained by adding cysteine after 174-Pro of the C-terminal of G-CSF and covalently bonding branched PEG with 40 kDa to the same cysteine). Each isoform was diluted with PBS and administered to rats through the tail veins in a dose of 100 μg/kg based on the body weight measured upon the administration day. Administration was carried out only once upon the test day.

To provide analytic samples, 200 μl of blood was collected from the tail veins at a predetermined time depending on the constitution of a test group. In the case of the blank, blood sampling was performed before the administration. Sampling for PD/PK analysis was performed 7, 24, 48 and 72 hours after the administration. Neutrophils were counted in each blood sample to determine the in vivo activity.

Additionally, each blood sample was introduced into an EDTA anticoagulant tube and subjected to centrifugal separation to separate blood plasma. G-CSF concentration in the plasma was measured by using a human G-CSF ELISA kit (Quantokine, R&D Systems). Each sample was diluted serially to the linear zone allowing detection of concentration in the kit. Measurement was performed two times per sample. The results are shown in the following Table 3.

As can be seen from Table 3, the polyethylene glycol-bound human granulocyte colony stimulating factor isoforms having cysteine added to the N-terminal or C-terminal according to the present invention shows an increased in vivo activity and in vivo lifetime. In particular, N+20 kDA(Br) and 175C+20 kDa(Br) show a significant increase in activity from the point of 24 hours after the administration, when compared to the control. Additionally, 175C+40 kDa(Br) shows an increase in activity from the point of 24 hours after the administration and a similar aspect of neutrophil production, when compared to the control. However, 175C+40 kDa (Br) can maintain its activity until the time of 72 hours after the administration. Particularly, 175C+40 kDa(Br) provides a significantly improved lifetime, while 175C+20 kDa(Br) and N+20 kDa(Br) provide a significantly improved activity.

TABLE 3

| Time | Carrier | Neulasta | N + 20 kDa (Br) | T133C20 kDa (Br) | 175C + 20 kDa (Br) | 175C + 40 kDa (Br) |
|---|---|---|---|---|---|---|
| 0 | 1.31 | 0.94 | 0.87 | 1.03 | 1.19 | 1.52 |
| 24 | 1.77 | 12.5 | 12.78 | 11.33 | 12.8 | 11.5 |
| 48 | 0.99 | 12.5 | 16.51 | 6.84 | 17.25 | 10.92 |
| 72 | 1.43 | 2.31 | 2.35 | 4.21 | 4.32 | 9.83 |

INDUSTRIAL APPLICABILITY

As can be seen from the foregoing, the human granulocyte colony stimulating factor isoforms according to the present invention provide a significantly increased in vivo lifetime and can be used for treating or preventing various human granulocyte colony stimulating factor-related diseases.

While this invention has been described in connection with what is presently considered to be the most practical and preferred embodiment, it is to be understood that the invention is not limited to the disclosed embodiment and the drawings. On the contrary, it is intended to cover various modifications and variations within the spirit and scope of the appended claims.

The invention claimed is:

1. A granulocyte colony stimulating factor isoform, which includes at least one amino acid added before Thr of N-terminal or after Pro of C-terminal in human granulocyte colony stimulating factor (SEQ ID NO:1) wherein at least one of the added amino acids is cysteine, and wherein a branched polyethylene glycol is bound to a cysteine of the isoform protein.

2. The granulocyte colony stimulating factor isoform according to claim 1, wherein the polyethylene glycol has a molecular weight of 20 kDa~40 kDa.

3. A granulocyte colony stimulating factor isoform, wherein 133-threonine of the granulocyte colony stimulating factor (SEQ ID NO:1) is substituted with cysteine, and wherein a branched polyethylene glycol is bound to a cysteine of the isoform protein.

4. The granulocyte colony stimulating factor isoform according to claim 3, wherein the polyethylene glycol has a molecular weight of 20 kDa~40 kDa.

* * * * *